(12) United States Patent
Harnack et al.

(10) Patent No.: US 7,858,393 B2
(45) Date of Patent: Dec. 28, 2010

(54) METHOD TO DRY MICROTITRATION FILTER TRAY CAVITIES AND RECEIVED FILTERS THEREIN

(75) Inventors: Kurt Harnack, Tangstedt (DE); Peter Scheffler, Hamburg (DE)

(73) Assignee: Eppendorf AG, Hamburg (DE)

( * ) Notice: Subject to any disclaimer, the term of this patent is extended or adjusted under 35 U.S.C. 154(b) by 918 days.

(21) Appl. No.: 11/279,125

(22) Filed: Apr. 10, 2006

(65) Prior Publication Data

US 2006/0242857 A1    Nov. 2, 2006

(30) Foreign Application Priority Data

Apr. 11, 2005    (DE) .................. 10 2005 016 755

(51) Int. Cl.
*F26B 5/04*   (2006.01)
*B01L 3/00*   (2006.01)
*G01N 1/00*   (2006.01)

(52) U.S. Cl. ................ 436/176; 422/102; 34/402

(58) Field of Classification Search .......... 422/102; 34/402; 436/176
See application file for complete search history.

(56) References Cited

U.S. PATENT DOCUMENTS

| | | | |
|---|---|---|---|
| 3,847,200 A * | 11/1974 | Kopp et al. ................ 159/16.1 |
| 5,324,483 A * | 6/1994 | Cody et al. ................ 506/40 |
| 5,380,437 A | 1/1995 | Bertoncini | |
| 5,459,300 A * | 10/1995 | Kasman ................ 219/433 |
| 5,681,492 A * | 10/1997 | Van Praet ................ 219/400 |
| 6,054,100 A * | 4/2000 | Stanchfield et al. .......... 422/102 |
| 6,159,368 A * | 12/2000 | Moring et al. ........... 210/321.75 |
| 6,274,091 B1 | 8/2001 | Mohan et al. | |
| 6,419,827 B1 * | 7/2002 | Sandell et al. .......... 210/321.75 |
| 6,592,826 B1 | 7/2003 | Bloecker et al. | |
| 2004/0033619 A1 | 2/2004 | Weinfield et al. | |
| 2006/0171850 A1 * | 8/2006 | Waterbury et al. ........... 422/100 |

FOREIGN PATENT DOCUMENTS

| | | |
|---|---|---|
| DE | 4031500 | 4/1992 |
| DE | 4316163 | 11/1994 |
| DE | 19725894 | 12/1998 |
| DE | 1174703 | 1/2002 |
| DE | 10144225 | 2/2003 |
| EP | 1257363 | 11/2002 |

* cited by examiner

*Primary Examiner*—Jill Warden
*Assistant Examiner*—Dean Kwak
(74) *Attorney, Agent, or Firm*—Rankin, Hill & Clark LLP

(57) ABSTRACT

An apparatus for drying microtitration filter tray cavities and filters configured therein using a flow of gas, the cavities each comprising an upper and a lower aperture and the microtitration filter tray being mounted on a chamber designed for the vacuum filtration of microtitration filter trays in a manner that a vacuum can be applied to the lower apertures of the cavities receiving the filters, and includes a heat exchanger which can be mounted on and later removed from the microtitration filter tray and can be heated and comprises at least one inlet aperture and at least one outlet aperture between which a flow of gas may move through the heat exchanger, the heat exchanger being designed to heat the gas flow and to guide it onto the upper cavity apertures, the gas flow being generated by a vacuum pump communicating with the vacuum chamber.

3 Claims, 3 Drawing Sheets

METHOD TO DRY MICROTITRATION FILTER TRAY CAVITIES AND RECEIVED FILTERS THEREIN

BACKGROUND OF THE INVENTION

The present invention relates to apparatus for drying cavities in microtitration filter trays and filters received therein, further to a system incorporating such apparatus, and to a method to dry microtitration filter trays and filters received therein.

Apparatus, systems and methods of this kind are used in particular when processing liquid test samples, mostly contained in buffers in microtitration filter trays.

Conventional microtitration filter trays are fitted, for instance, with 96 cavities each presenting an upper and a lower aperture, a filter being configured in the region of the lower aperture and covering its cross-section.

The samples are pipetted into the individual microtitration filter tray cavities and then are aspirated by vacuum filtration through the filters and thereby are separated into components. If the components absorbed in the filters are found to be significant, then in most instances, following test sample filtration, a washing solution will be applied several times into the cavities and will be aspirated through the filters. Next, an elution buffer is used to remove the significant components of the liquid test samples from the filter. Accordingly, conventional processing entails moving different liquids sequentially through the filters configured in the microtitration filter tray cavities.

A problem is encountered, in particular, when using buffering or washing solutions containing an alcohol or other organic solvents (isopropanol) that are miscible with water on account of the solvents fixating in the filter capillaries and possibly then interfering with subsequent reactions. Also, residues of the solvent that was used remain as drops on the cavity side walls, especially at the exit side underneath the filters.

As a result, between filtration stages, especially when alcohol-containing buffers or washing solutions are employed, the particular residual liquid ought to be removed each time. This desideratum also applies to the drops on that cavity wall. Consequently, a drying procedure usually is used in the state of the art.

A number of methods to dry cavities and the filters of a microtitration filter tray are known. The simplest one, which however entails prohibitively time-consuming process steps, would be to let the microtitration filter tray stand a long enough time to allow the residual liquid, in particular a substantially volatile alcohol, to evaporate into the ambient air.

Evaporation might be accelerated by heating the microtitration filter tray. Such a design is illustratively shown in the US patent document 2004/0033619 A1 and in the European patent document EP 1257363 B1. It was noted however that relatively high temperatures are needed to assure good drying of the cavities and filters. Such high temperatures, in turn, may damage the microtitration filter tray and also be injurious to the samples.

It is further known to dab off the cavities and filters with absorbent paper. While dabbing may be automated and in fact is very effective on the drops remaining on the cavity walls, on the other hand it only removes the residual liquid on or near the filter surface. More deeply imbedded residual liquid cannot be removed in this manner.

Again, the residual liquid in the cavities and filters might be eliminated by centrifuging. This approach entails the drawback of having to remove the microtitration filter tray out of the vacuum chamber and place it in a centrifuge. Such an additional operational step is undesirable, especially as regards method automation.

It is further known from the German patent DE 101 44 225 C1 to apply an airflow through the upper cavity apertures to the filters. However, this method is fairly time-consuming.

BRIEF SUMMARY OF THE INVENTION

The objective of the present invention is to create an apparatus and a method to dry microtitration filter tray cavities and the filters configured therein, the apparatus and method being applicable in a simple and effective manner without being unduly time-consuming. In particular, the present invention shall create apparatus which can be integrated in an automated mode in a simple manner into conventional vacuum filtration chambers.

The apparatus of the present invention dries the cavities of a microtitration filter tray and the filters therein by means of a heated flow of gas and is characterized by a heat exchanger that is attachable to and then removable from the tray. This heat exchanger may be deposited on the tray or it may be kept by a suitable affixation device at a space above it. The heat exchanger may be heated and it comprises at least one inlet aperture and one outlet aperture for gas flow and it heats the gas flow passing through the tray and guides the flow onto the upper cavity apertures. This gas flow is generated by a vacuum pump to which a chamber designed to vacuum-filter trays is connected, the microtitration filter tray being arranged on this chamber. In this manner a heated gas, for instance air, sweeps the cavity walls and arrives at the filters to be dried, i.e., it is aspirated by the vacuum pump through the filters to be dried.

The cavities and the filters can be dried in especially a simple and effective manner by the apparatus of the present invention.

In principle, the heat exchanger design may be arbitrary as regards shape and size. Preferably, however, the features of the invention are used in order to improve handling and automation. If the heat exchanger length and width are conventional, for instance for microtitration filter trays, it may be deposited on them. Where called for, it may be handled with the same fasteners and transport elements that are used for handling the trays.

Among other advantages, the need for additional heat exchanger fasteners is eliminated. Because of the heat insulation, the heated heat exchanger may rest on the microtitration filter tray, for instance with an air gap between them, no damages being incurred by the tray. On the other hand, the seal advantageously precludes aspirating extraneous, unheated air that would degrade drying. The gas flow arriving at the filters reliably crosses the heat exchanger and is heated in that process. The seal need not be hermetic. Simple seals already allow for substantially reducing the proportion of extraneous air.

Suitable sealing and insulating elements, illustratively, may be fitted on the microtitration filter tray. Alternatively, the tray and the heat exchanger may be mounted in a support holding both in a sealing and thermally insulating manner. The heat exchanger is fitted radially outward on its side facing the microtitration filter tray with a heat-resistant seal configured against the side. Consequently, the apparatus is applicable to conventional microtitration filter trays, while supports of complex designs are not needed. On the contrary, the heat exchanger so designed may be used as a further accessory for conventionally known laboratory automated equipment.

The apparatus of the present invention is detachable for instance for the purpose of not hampering further procedures after drying, such as filling the cavities with new test sample liquids. In one simple implementation of the present invention, for instance, the operator can remove the heat exchanger which is fitted for that purpose, for instance with thermally insulated grip elements, to secure the operator against burns at the hot heat exchanger. However, advantageous features allow the automated heat exchanger to operate, for instance, in known automated laboratory equipment. For that purpose the heat exchanger is designed to be moved by means of an associated transporter. As a rule automated laboratory equipment are fitted with transporters, illustratively to allow moving the microtitration filter trays. The transporters also may be used to transport the heat exchanger. In particular, when the heat exchanger's length and width correspond to a conventional microtitration filter tray, transporter control need only operate as called for at an altered height coordinate relative to transporting a microtitration filter tray. However, the apparatus of the present invention also may be operated when it is fitted with its own transporter.

Illustratively the heat exchanger may be heated in an active manner, that is, it may be fitted with its own heater. This heater illustratively may be connected by a cable to a power source. Again, illustratively, the heat exchanger may also be fitted with electrical terminals that shall make electrical contact with mating terminals when the heat exchanger is mounted on the microtitration filter tray, thereby applying electric power to the heater which then can heat the heat exchanger. In this manner a potentially interfering cable connection to the heat exchanger may be eliminated. However, the heat exchanger may be heated in a heating position in which the heat exchanger is moveable by the transporter and, for instance, the aforementioned heat exchanger terminals make contact with mating terminals. In particular, the heat exchanger, when in the heating position, may be heated passively by being deposited on a thermostatting unit. As regards passive heating, a thermostatting unit, that is generally available anyway in automated laboratory equipment, may be used. This feature offers the special advantage that the heat exchanger may be heated before being required to heat the gas flow. In this manner a heating interval following deposition on the microtitration filter trays is eliminated. The advantage of passive heating is the simpler heat exchanger design, for instance it being a planar structure.

Illustratively, the heat exchanger may be an open-pore material such as a sintered or a frothed metal. The outlet apertures are designed as nozzles of which at least one is associated with each cavity and which are configured in the cavity pattern, thereby allowing good guidance of the heated gas flow onto the cavities and onto the filters. Illustratively, in one embodiment variation, the nozzles may be boreholes in the heat exchanger that for instance may be open pores filled with fine metal particulates. The concept of "nozzle" in this application of the invention shall be any device implementing a directed airflow.

When several nozzles are allocated to each cavity, the heat-transferring heat exchanger surface in contact with the flow of gas is increased, thereby more heat per unit time being transferred to the gas passing through. Drying time is reduced.

The features of the invention offer the advantage that the flow impedance of the heat exchanger is a small fraction of that of the filters and consequently the suction performance of the vacuum pump generating the flow of gas is predominantly determined by the filter flow impedance. In some adverse circumstances, an increase in required suction may damage the microtitration tray. Furthermore, the proportion of undesired extraneous air increases with increasing heat exchanger flow impedance, and in some cases the costs of sealing against extraneous air would then have to be increased.

In addition to the above described apparatus, the invention also comprises a vacuum chamber designed for vacuum filtration and a vacuum pump communicating with the vacuum chamber. Illustratively, the components might be the chambers and pumps present in conventional automated laboratory equipment which, when applied to the system of the invention, would need completion only by an apparatus as defined herein.

BRIEF DESCRIPTION OF THE DRAWINGS

The invention is elucidated by means of the FIGS. 1 through 3 showing several illustrative embodiments.

DETAILED DESCRIPTION OF THE INVENTION

Figure 1:
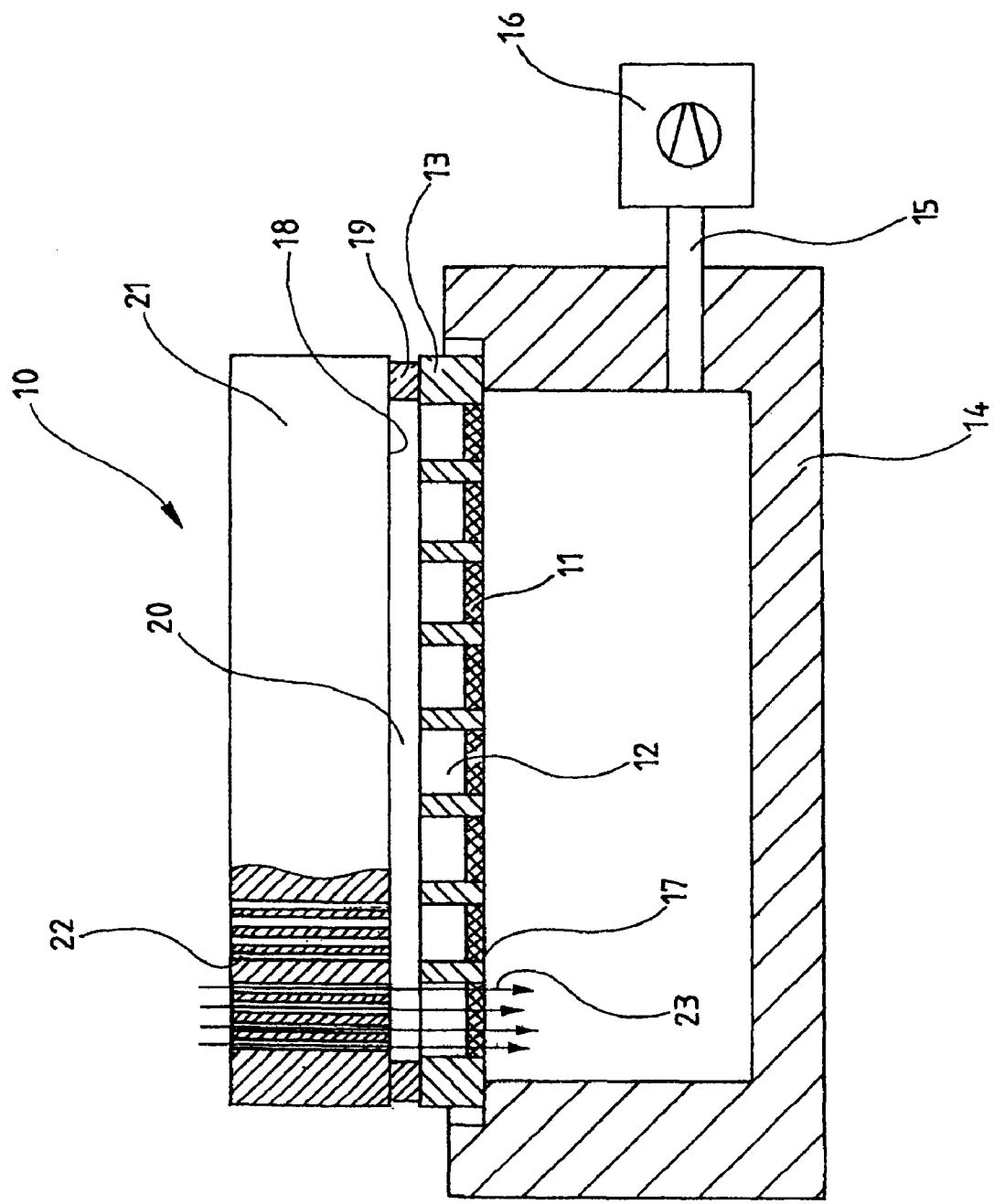
FIG. 1 is a cross-sectional view of a first illustrative embodiment of an apparatus of the invention within the drying position.

FIG. 1 is a cross-sectional and schematic view of an apparatus 10 for drying cavities 12 and filters 11 configured in cavities 12 of a microtitration filter tray 13. The microtitration filter tray 13 rests on a conventional chamber 14 used for vacuum filtration. A vacuum can be applied by a vacuum pump 16 connected through a conduit 15 with the chamber 14 to the lower apertures 17 of the cavities 12.

For the purpose of drying the filters 11 and cavities 12, the apparatus 10 will be deposited on the microtitration filter tray 13. The apparatus 10 consists of a heat exchanger 21 which is fitted at its underside 18 with an insulating ring 19. This insulating ring 19 is situated radially outward at the underside 18 of the heat exchanger 21 and is made of a material withstanding the temperatures arising at the heat exchanger 21. The insulating ring 19 thermally separates the heat exchanger 21 from the microtitration filter tray 13 and subtends between them an air-filled gap 20.

Besides its thermally insulating function, the insulating ring 19 is also designed to laterally and hermetically seal the space 20 to preclude aspirating extraneous air.

The heat exchanger 21 is deposited on the microtitration filter tray 13 and is heated ahead of the drying procedure on a heater, omitted from FIG. 1. Then the vacuum-applying vacuum pump 16 is turned ON. As a result a vacuum is set up in the chamber 14 and hence at the lower apertures 17 of the cavities 12. This vacuum entails aspirating through the permeable filters 11 the air contained in the chamber 20. The ensuing flow of air moves through the cavities 12 of the microtitration tray 13 and through the permeable filters 11. The space 20 between the heat exchanger 21 and the microtitration filter tray, being laterally hermetically sealed by the insulating ring 19, thus, air is aspirated from above the heat exchanger 21 through its boreholes 22 and this air is heated while flowing through the heat exchanger 21. Therefore a flow of air 23 moves through the heat exchanger 21, the space 20 and the cavities 21, whereby the filters 11 and the cavities 12 are crossed by heated air and are dried by it.

The pump 16 may be shut off at the end of the drying procedure and the heat exchanger 21 can be removed, for instance, to fill the cavities 12 with new sample liquid.

In the illustrative embodiment shown, the heat exchanger is designed as a plate having the same base surface as the microtitration filter tray 13. The boreholes 22 run from the top to the underside 18 of the plate 21 and are configured in the pattern of the cavities 12 of this microtitration filter tray 13, a set of 4×4 boreholes 22 being allocated to each cavity 12.

Figure 2:
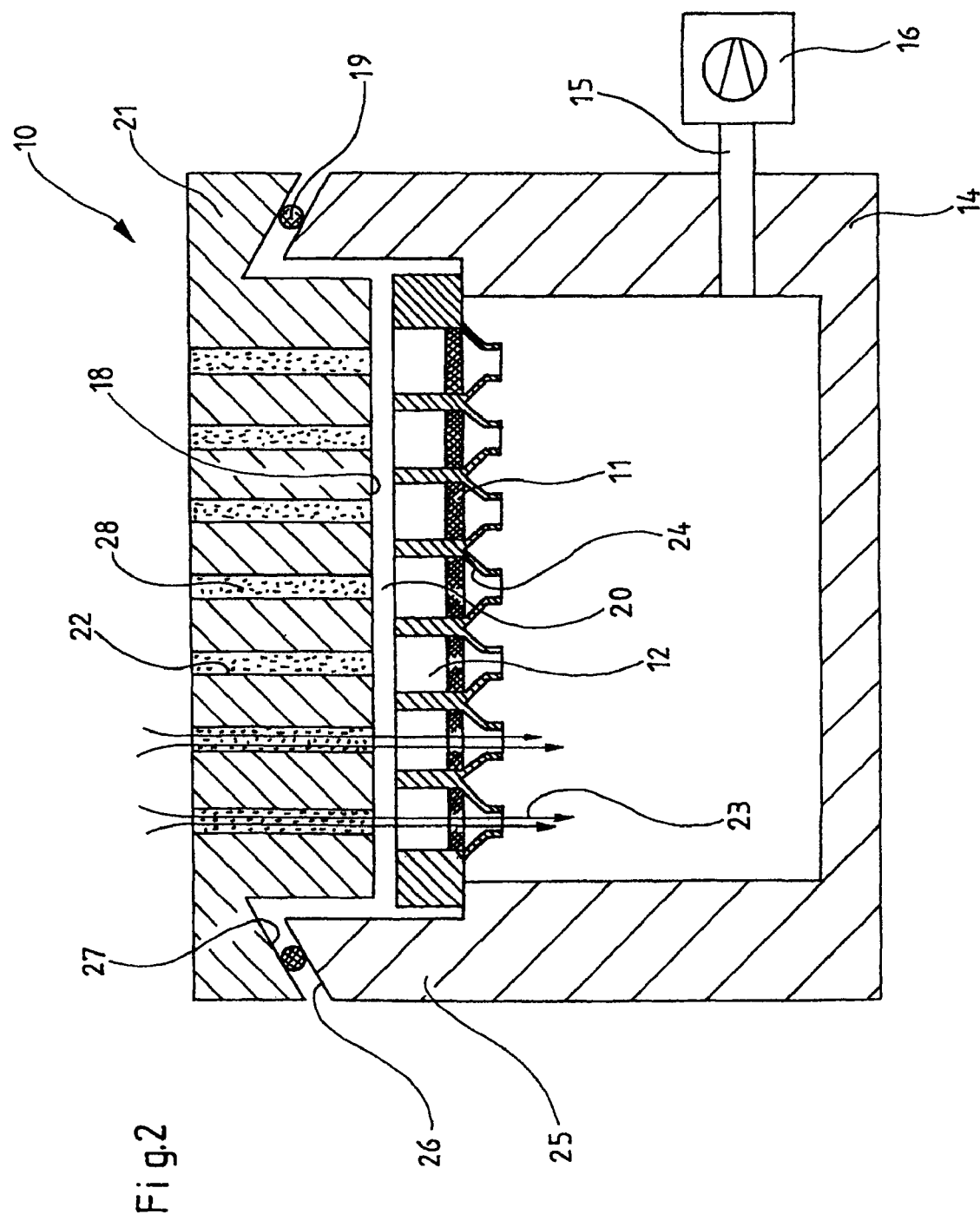
FIG. 2 is a cross-sectional view of a second illustrative embodiment of an apparatus of the invention.

In the illustrative embodiment shown in FIG. 2, the heat exchanger 21, unlike that of FIG. 1, does not rest on the microtitration filter tray 13 but instead is configured a slight height above the tray by the sidewalls 25 of the vacuum chamber 14. The mutually opposite end faces 26, 27 of the raised sidewall 25 of the vacuum chamber 14 and of the heat exchanger 21 are separated in this embodiment by a sealing ring 19 affixed to the heat exchanger 21 and sealing the space 20 enclosed between the heat exchanger 21, the microtitration filter tray 13 and the sidewall 25 of the vacuum chamber 14 against extraneous air. The seal 19 moreover provides thermal insulation to prevent the sidewall 25 of the chamber 14 from dissipating heat from the heat exchanger 21.

In this embodiment too the heat exchanger 21 is fitted with boreholes 22 running from its top side to its bottom side 18 and being filled with metal particulates 28 enhancing the heat dissipating contact area with the gas 23 flowing through the boreholes 22. In this embodiment mode too the gas flow 23 is produced by a vacuum pump 16 of the kind already discussed in relation in FIG. 1.

The cavities 12 of FIG. 2 are narrow and funnel-shaped underneath the filters 11. Solvent residues, in the form of droplets, remain in particular, at the sidewalls 24 of this funnel-shaped zone and must be removed before the next reactions will be carried out. The heated air passing through the filters 11 sweeps the walls 24 in this zone and causes the droplets to evaporate whereby both the filters shall be dried and also the cavity walls above and especially below the filters 11 shall be dried.

Figure 3:
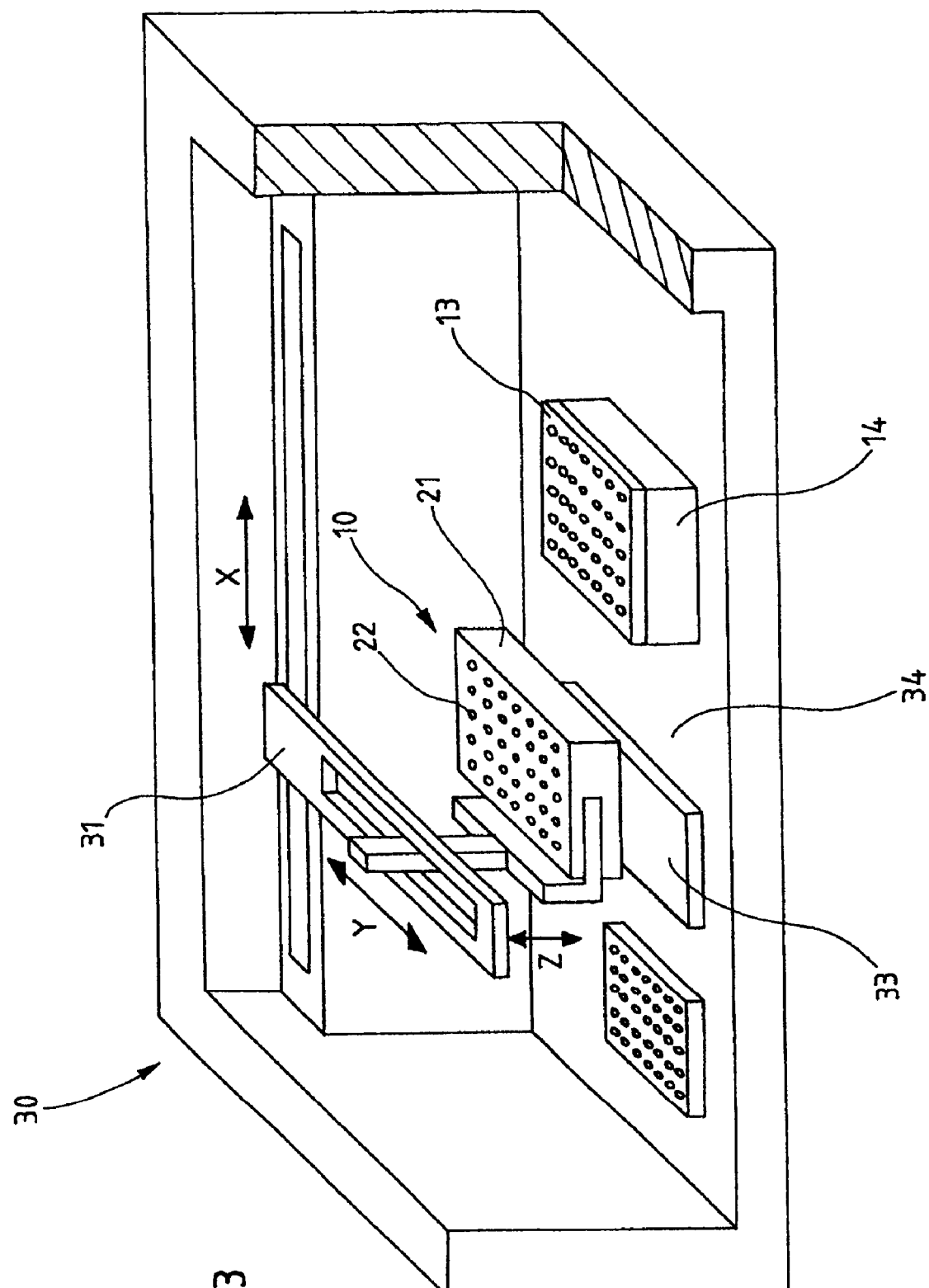
FIG. 3 is a perspective and schematic view of an automated laboratory equipment fitted with an illustrative embodiment of the invention.

Lastly FIG. 3 shows the basics of automated laboratory equipment 30. This automated equipment 30 is fitted with a transporter 31 comprising a gripper 32 displaceable in the x, y and z directions. This gripper 32 is able to grip microtitration filter trays, and also the heat exchanger. In the shown snapshot, the heat exchanger 21 previously heated on the heating plate 33 is being moved toward the microtitration tray 13 configured on a vacuum chamber 14 such as illustratively shown in FIG. 1. The heat exchanger 21 will be deposited at that site and drying may then begin. Following drying the heat exchanger 21 may be removed and for instance may be deposited again on the heating plate 33.

In preparation of drying, the heat exchanger 21 first is deposited for a heating time interval in the heating position 34 on the heating plate 33. This position also may be the rest position of the heat exchanger 21, and the automated equipment 30, illustratively, may be operated to turn ON the heating plate 33 shortly before the heat exchanger 21 is needed for the drying procedure. Thereupon the transporter 31, by means of its gripper 32, grips the heat exchanger 21, moves it onto the microtitration filter tray 13 resting on the vacuum chamber 14 and then from above deposits the exchanger. A gas flow may then be generated as described in relation to FIGS. 1 and 2. The gas flowing from the outside through the heat exchanger 21 is then heated and moves through the cavities 12 of the microtitration filter tray 13 and through the filters 11 configured therein.

The invention claimed is:

1. A method for handling a microtitration tray (13) with cavities (12) each comprising an upper aperture and a lower aperture (17) receiving filters (11) within the cavities (12), comprising the steps of:
    (1) configuring the microtitration filter tray (13) on a chamber (14) designed for vacuum filtration of microtitration filter trays (13);
    (2) pipetting samples into the individual microfiltration filter tray cavities (12);
    (3) aspirating the samples through the filters (11) by applying a vacuum to the lower apertures (17) of the cavities (12) receiving the filters (11);
    (4) applying several times a washing solution into the cavities (12) and aspirating the solution through the filters (11) and/or using an elution buffer to remove significant components of the samples from the filters (11);
    (5) mounting a heat exchanger (21) detachably on the microtitration filter tray (13) which is either heated before being mounted or is heated after being mounted, said heat exchanger (21) comprising at least one inlet aperture and at least one outlet aperture (22) allowing a gas flow (23) to move between them; and
    (6) generating a gas flow to pass through the filters (11) by a vacuum pump (16) communicating with the vacuum chamber (14) using said heat exchanger (21) to heat the gas flow (23) and guide the gas flow to the upper apertures of the cavities (12), the gas flow (23) moving from the inlet aperture to the outlet aperture of said heat exchanger (21).

2. The method as claimed in claim 1, further including the step of displacing the heat exchanger (21) between a heating position (34) and the position on the microtitration filter tray (13), in automated manner by an associated transporter (31, 32).

3. The method as claimed in claim 2, wherein the heat exchanger (21) is heated passively and when in a heating position (34) makes contact over a large area with a thermostatting unit (33).

* * * * *